(12) United States Patent
Takase

(10) Patent No.: US 6,773,395 B2
(45) Date of Patent: Aug. 10, 2004

(54) ENDOSCOPE

(75) Inventor: Seisuke Takase, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 09/947,680

(22) Filed: Sep. 6, 2001

(65) Prior Publication Data

US 2002/0072654 A1 Jun. 13, 2002

(30) Foreign Application Priority Data

Sep. 8, 2000 (JP) ........................................ 2000-273793

(51) Int. Cl.⁷ ................................................ A61B 1/04
(52) U.S. Cl. ........................ 600/133; 600/139; 600/153
(58) Field of Search ................................ 600/133, 139, 600/140, 141, 142, 143, 144, 153, 156

(56) References Cited

U.S. PATENT DOCUMENTS 4,756,303 A * 7/1988 Kawashima et al. ........ 600/139
5,394,864 A * 3/1995 Kobayashi et al. ......... 600/146
5,810,713 A * 9/1998 Rondeau et al. ............ 600/133
5,876,331 A * 3/1999 Wu et al. .................... 600/139
5,885,209 A * 3/1999 Green ......................... 600/153
6,419,628 B1 * 7/2002 Rudischhauser et al. .... 600/161
6,565,507 B2 * 5/2003 Kamata et al. ............. 600/153

FOREIGN PATENT DOCUMENTS

JP 8-136823 5/1996
JP 10-276968 10/1998

* cited by examiner

Primary Examiner—Beverly M. Flanagan
(74) Attorney, Agent, or Firm—Scully, Scott, Murphy & Presser

(57) ABSTRACT

An endoscope of the present invention includes a flexible tube section having an outer sheath layer composed of resin for constituting an endoscope insertion section and a slender tube member inserted into the endoscope insertion section, wherein the amount of shrink of the tube member after the completion of a high temperature/high pressure steam sterilization process is set as much as or greater than the amount of shrink of the flexible tube section after the completion of the high temperature/high pressure steam sterilization process.

10 Claims, 2 Drawing Sheets

ENDOSCOPE

This application claims benefit of Japanese Application No. 2000-273793 filed in Japan on Sep. 8, 2000, the contents of which are incorporated by this reference.

BACKGROUND OF THE INVENTION

1. Field of the Invention

The present invention relates to an endoscope that is sterilized with high pressure steam after it is used.

2. Description of the Related Art

Conventionally, there are widely used medical endoscopes capable of observing internal organs and the like in a body cavity by inserting a slender insertion section into the body cavity and executing various types of treatment and remedy using a therapeutic device inserted into a therapeutic device channel when necessary.

Endoscopes used in a medical field observe internal organs and the like by inserting an insertion section into a body cavity and execute various types of treatment and remedy using a therapeutic device inserted into the therapeutic device channel of the endoscopes.

When a once-used endoscope and a therapeutic device are to be used for other patient again, they must be washed and sterilized after the completion of checkup and treatment to prevent infection through the endoscope and the therapeutic device among patients.

Recently, autoclave sterilization (high pressure steam sterilization) is mainly used to disinfect and sterilize medical equipment because the autoclave sterilization permits the medical equipment to be used just after sterilization and its running cost is less expensive.

For example, Japanese Unexamined Patent Application Publication No. 10-276968 discloses an endoscope to which an annealed tube is assembled so that sufficient sterilization can be executed repeatedly while preventing the shrink of a tube contained in the endoscope when the endoscope is subjected to autoclave sterilization.

However, in the endoscope described above, the amount of shrink of the annealed tube inserted into an insertion section is smaller than that of a flexible tube section that is mainly composed of an outer sheath layer of resin. As a result, there is a possibility that the tube is loosened in the insertion section. Thus, there is also a possibility of causing disadvantages in that the loosened tube presses and bends a light guide cable and other members contained in the endoscope.

In addition to the above, when the temperature of the endoscope is returned to an ordinary temperature after it is released from a thermal load generated in a high temperature/high pressure steam sterilization process, if the tube meanders in a loosened state, the inner surface of the tube may be scratched or the tube itself may be broken when a forceps, a brush, or the like is inserted into the tube because an amount of force necessary to insert is increased.

OBJECTS AND SUMMARY OF THE INVENTION

An object of the present invention is to provide an endoscope which is unlikely to cause disadvantages in workability and handling by reducing looseness caused to a tube to be inserted into an insertion section when the endoscope is subjected to a thermal load in a high temperature/high pressure steam sterilization process.

Briefly, an endoscope of the present invention includes a flexible tube section having an outer sheath layer composed of resin for constituting an endoscope insertion section and a slender tube member inserted into the endoscope insertion section, wherein the amount of shrink of the tube member after the completion of a high temperature/high pressure steam sterilization process is set as much as or greater than the amount of shrink of the flexible tube section after the completion of the high temperature/high pressure steam sterilization process. Accordingly, when a thermal load is applied to the endoscope in the high temperature/high pressure steam sterilization process, it can be prevented that the tube member loosens and meanders in the flexible tube section and damages contained members by pressing them.

DETAILED DESCRIPTION OF THE PREFERRED EMBODIMENTS

An embodiment of the present invention will be described below with reference to the drawings.

The embodiment of the present invention will be described with reference to FIGS. 1 to 3.

Figure 1:
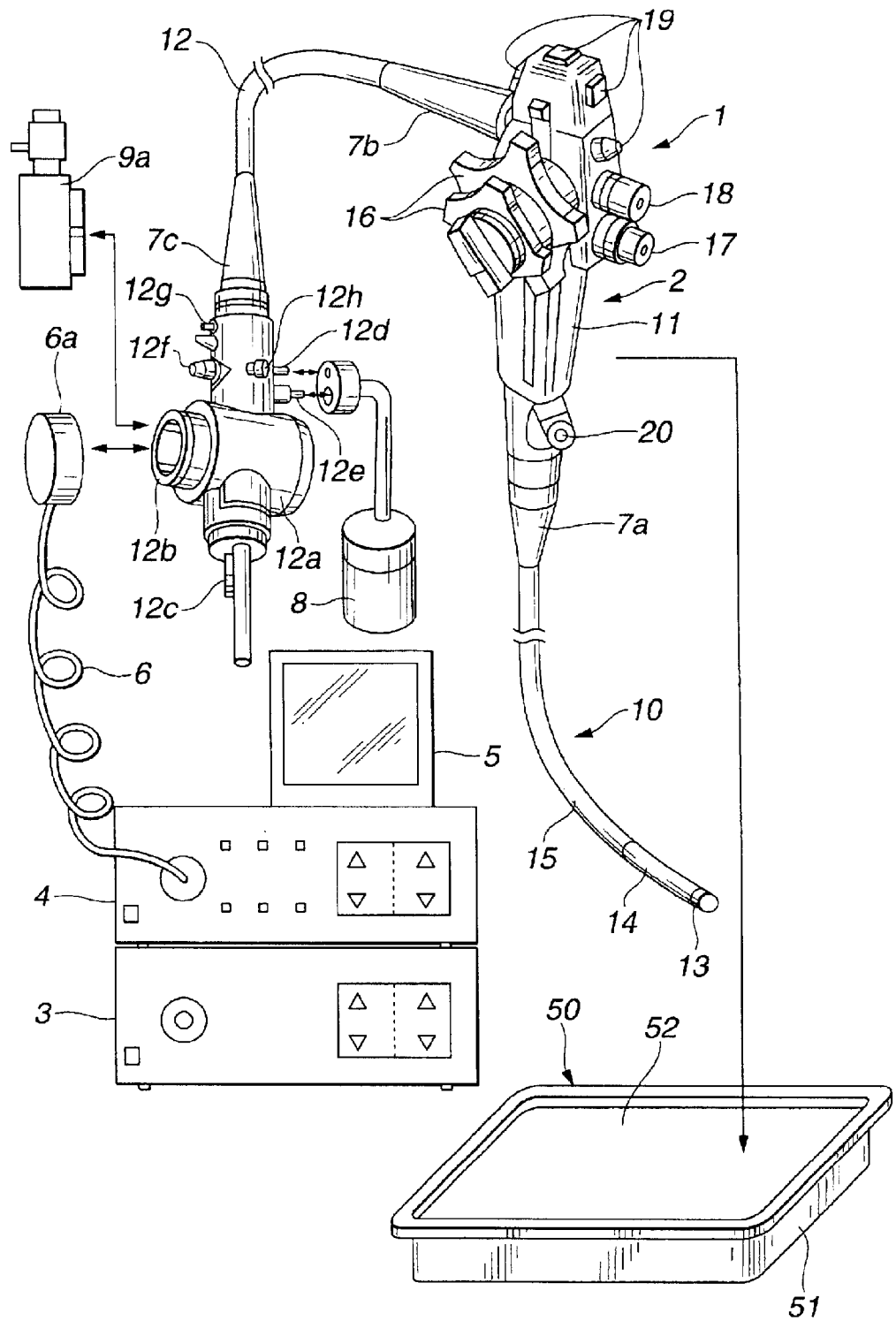
FIG. 1 is a view explaining the configuration of an endoscope device.

As shown in FIG. 1, an endoscope device 1 of this embodiment is mainly composed of an electronic endoscope (hereinafter, abbreviated as "endoscope") 2, a light source unit 3, a video processor 4, and a monitor 5.

The endoscope 2 includes an image pickup unit. The light source unit 3 supplies illumination light to the endoscope 2. The video processor 4 controls the image pickup unit and converts an image signal obtained by the image pickup unit to for example, a video signal. The video processor 4 is connected to the monitor 5. Note that reference numeral 50 denotes a sterilization accommodation case to be described later that acts as an endoscope accommodation unit for accommodating the endoscope 2 to be subjected to high temperature steam sterilization.

The endoscope 2 includes an insertion section 10, a manipulation unit 11, and a universal cord 12. The insertion section 10 is slender and flexible. The manipulation unit 11 is connected to the base end of the insertion section 10. The universal cord 12 is flexible and extends from a side of the manipulation unit 11.

A connector 12a that is detachably connected to the light source unit 3 is disposed to an end of the universal cord 12. Connection of the connector 12a to the light source unit 3 permits the illumination light from a lamp (not shown) mounted on the light source unit 3 to be transmitted to a light guide (not shown) in the endoscope 2 so that the illumination light illuminates a portion to be observed.

A manipulation unit bending prevention member 7a composed of an elastic member is disposed at the portion where the insertion section 10 is connected at the manipulation unit 11 to prevent them from being bent sharply. A manipulation unit bending prevention member 7b, which is arranged similarly to the bending prevention member 7a is also disposed at the portion where the manipulation unit 11 is connected to the universal cord 12. Moreover, a connector bending prevention member 7c arranged in the same manner is also disposed at the portion where the universal cord 12 is connected to the connector 12a.

The slender and flexible insertion section 10 of the endoscope 2 is arranged by sequentially connecting an extreme end hard portion 13, a curving portion 14, and a flexible tube section 15 acting as a soft portion from the extreme end thereof.

The extreme end hard portion 13 is composed of a hard member. An observation window, an illumination window, a gas/water supply nozzle for ejecting washing liquid and gas to the observation window, a suction port for sucking a body fluid, dirt and the like (all of the above are not shown) disposed at, for example, the extreme end surface of the extreme end hard portion 13.

The bending portion 14 is composed of a plurality of bending elements connected to each other so as to be free to bend.

The flexible tube section 15 has soft, elastic and delicate characteristics.

The manipulation unit 11 includes a bending manipulation knob 16 disposed thereto. Appropriate manipulation of the bending manipulation knob 16 causes the bending portion 14 to be bent in a desired direction. That is, the extreme end surface, where the observation window, and the like are disposed, of the extreme end hard portion 13 can be directed to a desired direction by bending the bending portion 14.

Note that a gas/water manipulation button 17, a suction manipulation button 18, a plurality of remote switches 19, . . . , 19 and a therapeutic device insertion port 20 are disposed at the manipulation unit 11 in addition to the above bending manipulation knob 16.

Appropriate manipulation of the gas/water manipulation button 17 causes washing liquid and gas to be ejected from the gas/water supply nozzle. Moreover, manipulation of the suction manipulation button 18 permits body fluid and the like to be sucked through the suction port. The plurality of remote switches 19, . . . , 19 control, for example, the video processor 4 remotely. The therapeutic device insertion port 20 communicates with a therapeutic device channel tube to be described later which is disposed in the insertion section of the endoscope 2.

The electric connector unit 12b is disposed at a side of the connector 12a. The signal connector 6a of a signal cord connected to the video processor 4 is detachably connected to the electric connector unit 12b. Connecting the signal connector 6a to the video processor 4 causes the image pickup unit of the endoscope 2 to be controlled as well as a video signal to be created from an image signal transmitted from the image pickup unit and an image observed through the endoscope to be displayed on the screen of the monitor 5.

A ventilation port (not shown) is disposed at the electric connector unit 12b to maintain communication between the inside and outside of the endoscope 2. Thus, a pressure-regulation-valve-mounted waterproof cap (hereinafter, abbreviated as "waterproof cap") 9a having a pressure regulation valve for closing the ventilation hole is detachably mounted on the electric connector unit 12b of the endoscope 2.

A gas supply mouth ring 12c, a water supply tank pressurizing mouth ring 12d, a liquid supply mouth ring 12e, a suction mouth ring 12f, a pouring mouth ring 12g, and a ground terminal mouth ring 12h are disposed at the connector 12a.

The gas supply mouth ring 12c is detachably connected to a gas supply source (not shown) contained in the light source unit 3. The water supply tank pressurizing mouth ring 12d and the liquid supply mouth ring 12e are detachably connected to a water supply tank 8 acting as a liquid supply source. The suction mouth ring 12f is connected to a suction source (not shown) for executing suction from the suction port. The pouring mouth ring 12g is connected to a water supply unit (not shown) for supplying water. An electric cable is connected to the ground terminal mouth ring 12h. With this arrangement, a high frequency leakage current generated when high frequency treatment and the like are executed can be fed back to a high frequency treatment device (not shown).

The endoscope 2 can be washed after it is used for observation and treatment and the endoscope 2 can be arranged so as to be subjected to high pressure steam sterilization. When the endoscope 2 is subjected to the high pressure steam sterilization, a waterproof cap 9a is mounted on the electric connector unit 12b. Moreover, when the endoscope 2 is subjected to the high pressure steam sterilization, the endoscope 2 is accommodated in the sterilization accommodation case 50.

The sterilization accommodation case 50 is composed of a tray 51 acting as a box member and a lid member 52 for closing the opening of the tray 51. Regulation members (not shown), which are formed in a shape corresponding to that of the endoscope 2, is disposed in the tray 51 to permit the respective units of the endoscope 2 such as the insertion section 10, the manipulation unit 11, the universal cord 12, the connector 12a, and the like to be accommodated at predetermined positions. Moreover, a plurality of ventilation holes are formed on each of the tray 51 and the lid member 52 to introduce high pressure steam into the sterilization accommodation case 50.

Figure 2:
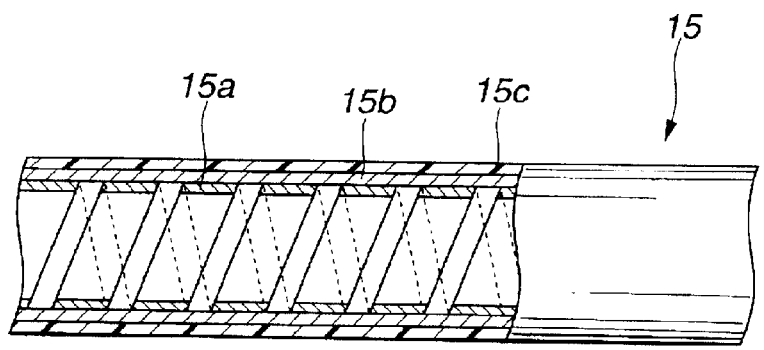
FIG. 2 is a view explaining the configuration of a flexible tube section.

As shown in FIG. 2, the flexible tube section 15 is composed of a spiral tube 15a, a mesh-like tube 15b, and an outer sheath layer 15c in which order they laminate therearound from the innermost layer side thereof. The spiral tube 15a is formed by winding a thin metal strip spirally. The mesh-like tube 15b is formed by knitting metal strands or non-metal strands. The outer sheath layer 15c is composed of, for example, thermoplastic ester type elastomer as a resin material.

Note that the outer sheath layer 15c may be formed of materials such as thermoplastic amide type elastomer, styrene type resin, fluorine type rubber, silicon rubber, or materials obtained by blending them, not limiting to the thermoplastic ester type elastomer.

Moreover, these resin materials used in the outer sheath layer 15c are selected in consideration of durability and insertion property when they are used and in consideration of chemical resistance to medicines, and the like which are used in washing and sterilization. Accordingly, some of the resin materials have a thermal deformation temperature which is lower than the temperature condition of a high temperature/high pressure steam sterilization process. Or, some of the resin materials are molded in a drawn state depending upon, for example, an extrusion molding condition when they are molded and deformed when they are released from the stress applied thereto when they are drawn.

Figure 3:
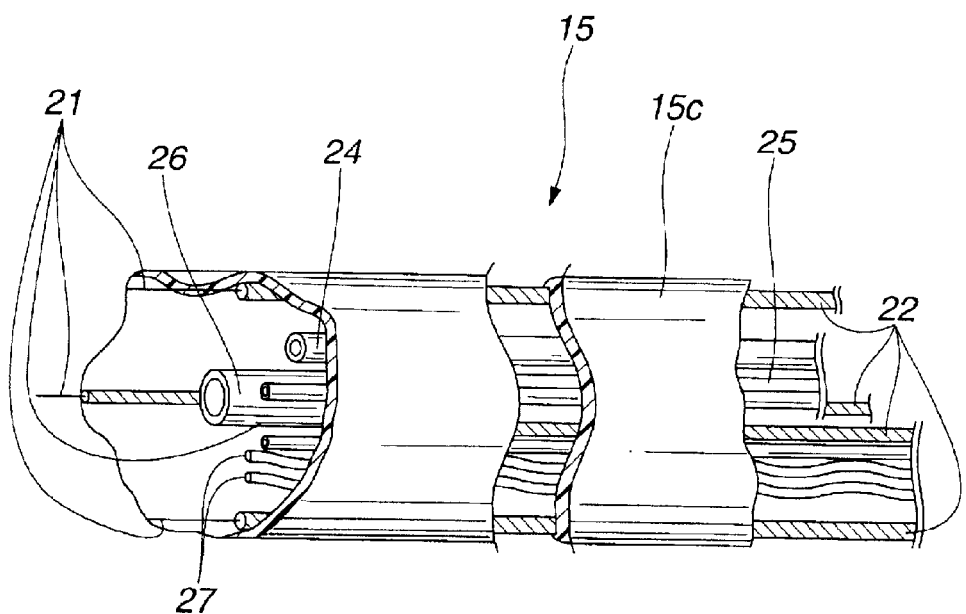
FIG. 3 is a view explaining the configuration of built-in members inserted into the flexible tube section.

As shown in FIG. 3, various contained members are inserted into the flexible tube section 15. These contained members are bent metal wires 21, wire-covered metal coils 22, a light guide 24, a gas/water supply tube 25, a therapeutic device insertion channel tube 26, signal cables 27, and the like.

The bent metal wires 21 are moved forward and backward by remotely manipulating the bending manipulation knob 16 so as to bend the bending portion 14. The wire-covered metal coils 22 cover the bent metal wires 21 in a loosely fitted state. The light guide 24 supplies illumination light. The gas/water supply tube 25 and the therapeutic device insertion channel tube 26 are composed of resin tube members.

The respective ends of the gas/water supply tube 25 and the therapeutic device insertion channel tube 26 are respectively locked and fixed to the connecting portion (not shown) of the manipulation unit 11 and to the connecting portion (not shown) of the extreme end hard portion 13, these connecting portions being coupled with both the ends of the insertion section 10.

The therapeutic device insertion channel tube 26 and the gas/water supply tube 25 are composed of a material having high chemical resistance such as PTFE or the like.

When the endoscope 2 is repeatedly sterilized in the high temperature/high pressure steam sterilization process, the flexible tube section 15, the therapeutic device insertion channel tube 26, and the gas/water supply tube 25 are shrunk in a lengthwise direction as compared with their initial state by the thermal load generated in the high temperature/high pressure steam sterilization process. An amount of shrink caused at this time corresponds to an amount of draw caused, for example, in the aforementioned molding.

In this embodiment, when the amount of shrink is set to $X_1$ in the therapeutic device insertion channel tube 26, to $X_2$ in the gas/water supply tube 25, and to Y in the flexible tube section 15, the relationship among these amounts of shrink are set to the following formula.

$$y \leq X_1, X_2$$

This means that a thermal load is applied to the flexible tube section 15 so as to release the stress thereof previously before the therapeutic device insertion channel tube 26 and the gas/water supply tube 25, for example, are assembled to flexible tube section 15 for the purpose of molding the flexible tube section 15 in the state that it has a high thermal deformation temperature and is unlikely to be affected by the thermal load.

Note that while the description of this embodiment is made as to the insertion section 10, a flexible tube section (not shown) constituting the universal cord 12 and the gas/water supply tube 25 as a contained member (not shown) to be inserted into the universal cord 12 also are arranged in the same manner.

Typical conditions under which the endoscope 2 is subjected to high pressure steam sterilization will be described here.

As the conditions, there is ANSI/AAMI ST37-1992 which is approved by American National Standards Institute and issued by Association for the Advancement of Medical Instrumentation. According to the Standard, the conditions are such that a sterilizing time is set to 4 minutes at 132° in a prevacuum type sterilization process and to 10 minutes at 132° in a gravity type sterilization process, respectively.

The temperature condition in a high pressure steam sterilization process is different according to a type of high pressure steam sterilization apparatus and a time set to a sterilization process. Ordinarily, the temperature is set in the range of about 115° to 138°. However, a temperature of about 142° can be set in certain types of sterilization apparatus.

On the other hand, the time in the high pressure steam sterilization process is different according to the temperature condition in the sterilization process. That is, the time is ordinarily set in the range of about 3 minutes to 60 minutes. Then, a time of about 100 minutes can be set in certain types of sterilization apparatus.

The pressure in a sterilization chamber is set to +0.2 Mpa with respect to the atmospheric pressure in the sterilization process.

Next, an ordinary prevacuum type high temperature/high pressure steam sterilization process for endoscope will be briefly described.

First, the waterproof cap 9a is mounted on the electric connector unit 12b of the endoscope 2 acting as equipment to be sterilized, and the endoscope 2 is accommodated in the sterilization accommodation case 50 and placed in a sterilization apparatus. Since the waterproof cap 9a is mounted on the electric connector unit 12b, the pressure regulation valve is closed and the ventilation port is closed thereby. That is, the inside of the endoscope 2 is hermetically sealed from the outside thereof in a watertight manner. Then, the inside of the sterilization apparatus is set to a pressure reduced state before the high temperature/high pressure steam sterilization process is executed (prevacuum process).

Note that the prevacuum process is a process for penetrating steam to the minute portions of the equipment to be sterilized in the sterilization process. In this prevacuum process, high pressure/high temperature steam is uniformly distributed to the entire equipment to be sterilized by reducing the pressure in the sterilization chamber. In the prevacuum process, the pressure in the sterilization chamber is ordinarily set to about −0.07 to −0.09 Mpa with respect to the atmospheric pressure.

When the pressure in the sterilization chamber is reduced in the prevacuum process, a pressure difference is made such that the external pressure of the endoscope 2 is lower than the internal pressure thereof. Thus, the pressure regulation valve of the waterproof cap 9a is opened, and the inside of the endoscope 2 is communicated with the outside thereof through the ventilation port. With this arrangement, it can be prevented that the pressure difference between the inside pressure of the endoscope 2 and the outside pressure thereof increases. That is, the endoscope 2 can be prevented from being broken by the pressure difference.

Next, the sterilization process for executing sterilization by supplying high temperature/high pressure steam into the sterilization chamber will be described.

In this sterilization process, the sterilization chamber is pressurized. Thus, a pressure difference is made such that the external pressure of the endoscope 2 is lower than the internal pressure thereof. As a result, the pressure regulation valve of the waterproof cap 9a is closed. With this operation, it can be prevented that high pressure steam penetrates into the inside of the endoscope 2 through the ventilation port.

However, high pressure steam gradually penetrates into the inside of the endoscope 2 through O-rings (not shown) and the like as a seal means formed of fluorine rubber, silicon rubber, or the like and disposed at the portion where the outer sheath layer 15c, which is formed of polymer, of the flexible tube section 15, and the outside package of the endoscope 2 are connected.

At this time, the pressure, which is obtained by adding the pressure reduced in the prevacuum process and the pressure increased in the sterilization process, is caused to the endoscope 2 from the outside to the inside.

Next, after the completion of the sterilization process, the sterilization chamber is evacuated again and a dry process is executed to dry the equipment having been sterilized.

In this dry process, drying of the endoscope 2 in the sterilization chamber is accelerated by exhausting steam from the sterilization chamber by evacuating the chamber.

In the dry process, the pressure in the sterilization chamber is ordinarily set to about −0.07 to −0.09 Mpa with respect to the atmospheric pressure. Note that the dry process is optionally executed when necessary.

In a pressure reduction process executed after the sterilization process, the pressure in the sterilization chamber is reduced and a pressure difference, in which the external pressure of the endoscope 2 is lower than the internal pressure thereof, is caused. Almost at the same time with the occurrence of the pressure difference, the pressure regulation valve of the waterproof cap 9a is opened, and the inside of the endoscope 2 is communicated with the outside thereof through the ventilation port. With this operation, the occurrence of a large pressure difference between the inside of the endoscope 2 and the outside thereof can be prevented.

Then, when the internal pressure of the endoscope 2 is approximately equal to the external pressure thereof, the pressure regulation valve of the waterproof cap 9a is closed. Then, the pressure reduction process is finished and the internal pressure of the apparatus is made equal to the atmosphere pressure.

Note that when the high pressure steam sterilization process is entirely finished, the pressure reduced in the pressure reduction process is applied to the outer package portion of the endoscope 2 from the outside to the inside thereof. Then, when the waterproof cap 9a is removed from the electric connector unit 12b, the inside of the endoscope 2 is communicated with the outside thereof through the ventilation hole. With this operation, the pressure in the interior of the endoscope 2 is made equal to the atmospheric pressure and the load applied to the outer package portion of the endoscope 2 by the pressure difference is removed.

As described above, when the endoscope 2 is repeatedly sterilized by the high temperature/high pressure steam sterilization process, the flexible tube section 15, the therapeutic device insertion channel tube 26, and the gas/water supply tube 25 are shrunk by the amounts of shrink of Y, X1, and X2, respectively.

At this time, since the relationship $Y \leq X1, X2$ is set among the amounts of shrink Y, X1, and X2 of the flexible tube section 15, when the flexible tube section 15 shrinks, the therapeutic device insertion channel tube 26 and the gas/water supply tube 25 shrink as much as or greater than the flexible tube section 15. Accordingly, the therapeutic device insertion channel tube 26 and the gas/water supply tube 25 do not loosen and meander in the flexible tube section 15.

Accordingly, the bent wire 21, the wire-covered metal coils 22, the light guide 24, the signal cables 27, and the like as other contained members are not pressed by the therapeutic device insertion channel tube 26 and the gas/water supply tube 25.

Moreover, therapeutic devices (not shown) and washing tools are often inserted into and removed from the therapeutic device insertion channel tube 26. Thus, if the therapeutic device insertion channel tube 26 loosens and meanders, an amount of force larger than necessary is required to insert and remove the therapeutic devices and the washing tools, and there is a possibility that the inside of the therapeutic device insertion channel tube 26 is damaged or buckled, and in the worst case, pierced and broken. In this embodiment, however, since no meander is caused in the therapeutic device insertion channel tube 26, a work for inserting therapeutic device and washing tool is not disturbed.

As described above, since the amounts of shrink of the therapeutic device insertion channel tube and the gas/water supply tube, which are inserted into and disposed in the flexible tube section are set as much as or greater than that of the flexible tube section, even if a thermal load is applied to the flexible tube section in the high temperature/high pressure steam sterilization process, it can be prevented that the therapeutic device insertion channel tube and gas/water supply tube loosen and meander in the flexible tube section. With this arrangement, it can be prevented that other contained members are pressed and damaged by the therapeutic device insertion channel tube and the gas/water supply tube.

Moreover, since the therapeutic device insertion channel tube does not loosen and meander, the good inserting property of therapeutic device and washing tool can be secured.

With the above arrangements, the occurrence of disadvantage to the contained members after the completion of high temperature/high pressure steam sterilization can be prevented as well as a work for inserting a therapeutic device, a work for washing the inside of the channel tube, and the like can be smoothly executed similarly before and after the high temperature/high pressure steam sterilization.

Note that when the therapeutic device insertion channel tube 26 and the gas/water supply tube 25 are locked and fixed to the connecting portions (not shown) of the insides of the insertion section 10 at both the ends thereof, they may be locked and fixed after they are previously loosened in such a degree that does not affect other contained members. At this time, the amount of looseness of each of the therapeutic device insertion channel tube 26 and the gas/water supply tube 25 is set to the amount of shrink which is caused to each of them when they are subjected to a thermal load in the high temperature/high pressure steam sterilization process.

With this arrangement, when the therapeutic device insertion channel tube 26 and the gas/water supply tube 25 are repeatedly subjected to thermal load in the high temperature/high pressure steam sterilization process and shrunk, tensile load applied to the therapeutic device insertion channel tube 26 and the gas/water supply tube 25 themselves can be reduced.

Moreover, the tensile load applied to the connecting portions where the therapeutic device insertion channel tube 26 and the gas/water supply tube 25 are fixed can also be reduced, whereby the durability of them can be improved.

It goes without saying that various different embodiments can be made based on the present invention within the wide range which does not depart from the spirit and scope of the invention.

Moreover, the present invention is by no means restricted to a particular one of the embodiments except that it is restricted by the accompanying claims.

What is claimed is:

1. An endoscope comprising:
    a flexible tube section having an outer sheath layer composed of resin for constituting an endoscope insertion section; and
    a channel tube provided in a space formed in said endoscope insertion section; and
    a light guide, bent metal wires and signal cables juxtaposed with the channel tube in the space;
    wherein the amount of shrink of said channel tube after the completion of a high temperature/high pressure steam sterilization process is greater than the amount of shrink of said flexible tube section after the completion of the high temperature/high pressure steam sterilization process.

2. An endoscope according to claim 1, wherein said tube member is a channel tube that constitutes a therapeutic device insertion channel.

3. An endoscope according to claim 1, wherein said tube member is a channel tube that constitutes a gas/water supply tube.

4. An endoscope according to claim 1, wherein said outer sheath layer comprises any of thermoplastic ester type elastomer, thermoplastic amide type elastomer, styrene type resin, fluorine type rubber, silicon rubber, and a material obtained by blending them.

5. An endoscope according to claim 1, wherein the temperature set in the high temperature/high pressure steam sterilization process is within the temperature range of about 115° C. to about 140° C.

6. An endoscope comprising:
   a flexible tube section having an outer sheath layer composed of resin for constituting an endoscope insertion section;
   a channel tube provided in a space formed in said endoscope insertion section; and
   a light guide, bent metal wires and signal cables juxtaposed with the channel tube in the space;
   wherein a thermal stress is applied to said flexible tube section so as to release the stress thereof previously, and molding said flexible tube section such that said flexible tube section has a high thermal deformation temperature and is unlikely to be affected by the thermal stress; and
   the amount of shrink of said channel tube after the completion of a high temperature/high pressure steam sterilization process is equal to or greater than the amount of shrink of said flexible tube section after the completion of the high temperature/high pressure steam sterilization process.

7. An endoscope according to claim 6, wherein said tube member is a channel tube that constitutes a therapeutic device insertion channel.

8. An endoscope according to claim 6, wherein said tube member is a channel tube that constitutes a gas/water supply tube.

9. An endoscope according to claim 6, wherein said outer sheath layer comprises any of thermoplastic ester type elastomer, thermoplastic amide type elastomer, styrene type resin, fluorine type rubber, silicon rubber, and a material obtained by blending them.

10. An endoscope according to claim 6, wherein the temperature set in the high temperature/high pressure steam sterilization process is within the temperature range of about 115° C. to about 140° C.

* * * * *